US010232010B2

(12) United States Patent
Gelder et al.

(10) Patent No.: US 10,232,010 B2
(45) Date of Patent: Mar. 19, 2019

(54) COMPOSITIONS AND METHODS FOR TREATMENT OF RADIATION EXPOSURE

(75) Inventors: Frank B. Gelder, Half Moon Bay (NZ); Gillian Alison Webster, Waiatarua (NZ)

(73) Assignee: Innate Immunotherapeutics Limited, Auckland (NZ)

( * ) Notice: Subject to any disclaimer, the term of this patent is extended or adjusted under 35 U.S.C. 154(b) by 1193 days.

(21) Appl. No.: 13/121,796

(22) PCT Filed: Sep. 30, 2009

(86) PCT No.: PCT/NZ2009/000207
§ 371 (c)(1),
(2), (4) Date: Jun. 13, 2011

(87) PCT Pub. No.: WO2010/039048
PCT Pub. Date: Apr. 8, 2010

(65) Prior Publication Data
US 2011/0236346 A1   Sep. 29, 2011

(30) Foreign Application Priority Data

Sep. 30, 2008 (NZ) ......................................... 571665

(51) Int. Cl.
| *A61K 38/00* | (2006.01) |
| *A61K 45/00* | (2006.01) |
| *A61K 38/05* | (2006.01) |
| *A61K 45/06* | (2006.01) |
| *A61N 5/10*  | (2006.01) |

(52) U.S. Cl.
CPC .............. *A61K 38/05* (2013.01); *A61K 45/06* (2013.01); *A61N 5/10* (2013.01); *A61N 2005/1094* (2013.01); *A61N 2005/1098* (2013.01)

(58) Field of Classification Search
CPC ........ A61K 38/20; A61K 38/05; A61K 38/19; A61K 35/28; A61K 35/14
See application file for complete search history.

(56) References Cited

U.S. PATENT DOCUMENTS

| 4,815,446 A | * | 3/1989 | McIntosh ........................... 600/3 |
| 5,877,147 A | * | 3/1999 | Pinegin ....................... 424/279.1 |
| 5,925,362 A | * | 7/1999 | Spitler et al. ............... 424/277.1 |

FOREIGN PATENT DOCUMENTS

| CN | 1234078 A | 11/1999 |
| WO | 9815658 A1 | 4/1998 |
| WO | WO1998/015658 | 4/1998 |
| WO | WO 9815658 A1 * | 4/1998 |

(Continued)

OTHER PUBLICATIONS

Kekkaku, "Muramyl dipeptide derivative and its clinical application." (Nov. 1989;64(11):731-9, Abstract Only).*

(Continued)

*Primary Examiner* — Joanne Hama
(74) *Attorney, Agent, or Firm* — Meunier Carlin & Curfman LLC

(57) ABSTRACT

The present invention relates to an immunostimulant and to the use of an immunostimulant in the form of a cross-linked muramyl dipeptide microparticle in the treatment of radiation exposure, radiation poisoning, and mitigating the toxic effects of radiotherapy.

23 Claims, 16 Drawing Sheets

(56) References Cited

FOREIGN PATENT DOCUMENTS

| WO | 0024378 A1 | 5/2000 |
| WO | WO 2009123481 A1 * | 10/2009 |

OTHER PUBLICATIONS

Tabata et al., (J Pharm Pharmacol. 1987. 39:698-704).*
Osada et al., (Infection and Immunity. Sep. 1982;37(3):1285-1288).*
Namba et al., (Vaccine. Oct. 1996;14(14):1322-6; Abstract Only).*
Yano et al., (Anticancer Res. Nov.-Dec. 1995; 15(6B):2883-7, Abstract only).*
Yokuchi et al., (Gan to Kagaku Ryoho. Oct. 1997;24(13):1967-73, Abstract only).*
Namba et al., (Vaccine. Mar. 1997;15(4):405-13).*
Parant et al., (J Infect Dis. Sep. 1978;138(3):378-86, Abstract only).*
Azuma "Synthetic Immunoadjuvants: Application to Non-Specific Host Stimulation and Potentiation of Vaccine Immunogenicity" Vaccine, 1992, vol. 10(14), pp. 1000-1006.
International Search Report for International Application No. PCT/NZ2009/000207. Australian Patent Office. dated Jan. 21, 2010.
Masihi et al. "Muramyl Dipeptide Inhibits Replication of Human Immunodeficiency Virus in Vitro," Aids Research and Human Retroviruses, 1990, vol. 6(3), pp. 393-399.
Azuma "Review: Inducer of cytokines in vivo: Overview of field and Romurtide Experience," International Journal of Immunopharmacology, 1992, vol. 10(3), pp. 487-496.
Database, WPI, Week 1990, 23 Thomson Scientific, London, GB; AN 1990-229805 & SE 8, 803 621 A (Carbomatrix AB) (Apr. 13, 1990).
Supplementary European Search Report, dated Jun. 6, 2012, received from the European Patent Office in connection with European Patent Application No. 09818038.3.
Kawamori et al. "Effectiveness of thrice-weekly injection of Romurtide for prophylaxis of leukocytepenia during radiation therapy," Gan to Kagaku Ryoho. Cancer & Chemotherapy 1994, vol. 21(7), pp. 1057-1062.
Morin et al. "Improved intracellular delivery of a muramyl dipeptide analog by means of nanocapsules," International Journal of Immunopharmacology, 1994, vol. 16(5-6), pp. 451-456.
Namba et al. "Enhancement of Platelet Recovery in X-Irradiated Guinea Pigs by Romurtide, a Synthetic Muramyl Dipeptide Derivative," Blood, 1994, vol. 83(9), pp. 2480-2488.
Puri et al. "Adjuvancy enhancement of muramyl dipeptide by modulating its release from a physicochemically modified matrix of ovalbumin microspheres, I. In vitro characterization," Journal of Controlled Release, 2000, vol. 69(1), pp. 53-67.
Puri et al. "An investigation of the intradermal route as an effective means of immunization for microparticulate vaccine delivery systems," Vaccine, 2000, vol. 18(23), pp. 2600-2612.
Tabata, et al. "Activation of macrophage in vitro to acquire antitumor activity by a muramyl dipeptide derivative encapsulated in microspheres composed of lactide copolymer," Journal of Controlled Release, 1987, vol. 6(1), pp. 189-204.
Tsubura et al. "Restorative Activity of Muroctasin on Leukopenia Associated With Anticancer Treatment," Drug Research, 1998, vol. 38(7A), pp. 1070-1074.
Turánek et al. "Stimulation of haemopoiesis and protection of mice against radiation injury by synthetic analogues of muramyldipeptide incorporated in liposomes," International Journal of Immunopharmacology, 1997, vol. 19(9-10), pp. 611-617.
Youan et al. "Poly(ϵ-caprolactone) microparticles containing muramyl dipeptide for oral controlled release of ajduvant," Journal of Controlled Release, 1997, vol. 48(2-3), p. 339.
Youan et al. "Protein-loaded poly(ϵ-caprolactone) microparticles. II. Muramyl dipeptide for oral controlled release of adjuvant," Journal of Microencapsulation, 1999, vol. 16(5), pp. 601-612.
Office Action issued in corresponding Chinese application No. 2009801387748, dated Dec. 5, 2012.
Office Action issued in corresponding Chinese application No. 2009801387748, dated Jun. 20, 2013.
Azuma, Ichiro. Review: Inducer of Cytokines In Vivo: Overview of Field and Romurtide Experience. Int. J. Immunopharmac. 14(3): 487-496. 1992.
Qi, Zirong. Biological Effects of MDP. Bulletin of the Academy of Military Medical Sciences. 6. 1985.
Zhong, Yingying. Overview of Natural Immunostimulatory Peptides. Journal of Chongqing University of Science and Technology. 7(2). 2005.
Office Action issued in corresponding Japanese application No. 2011-530016, dated Jan. 21, 2014.
Tsubura, Eiro. The 64th Annual Meeting President Lecture: Muramyl Dipeptide Derivative and Its Clinical Application. Kekkaku. 64(11). 1989.
Youan, Bbc et al. Poly(e-Caprolactone) Microparticles Containing Muramyl Dipeptide for Oral Controlled Release of Adjuvant. Journal of Controlled Release. 48: 339. 1997.
Morin, C. et al. Improved Intracellular Delivery of a Muramyl Dipeptide Analog by Means of Nanocapsules. Int. J. Immunopharmac. 16(5/6): 451-456. 1994.

* cited by examiner

COMPOSITIONS AND METHODS FOR TREATMENT OF RADIATION EXPOSURE

FIELD OF THE INVENTION

The present invention relates generally to an immunostimulant and in particular, to the use of an immunostimulant in the form of a cross-linked muramyl dipeptide microparticle in the treatment of radiation exposure, radiation poisoning, and mitigating the toxic effects of radiotherapy.

The invention has been developed primarily for use as a treatment for radiation exposure and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of common general knowledge in the field.

Exposure to radiation can, in some cases, lead to radiation poisoning, which is a form of damage to biological tissue due to an increased exposure to a source of ionising radiation. Radiation poisoning is generally used to refer to the acute problems caused by a large dose of radiation over a short period of time, although this can occur with long term exposure to low level radiation. Many of the symptoms of radiation poisoning are due to the interference of ionising radiation with cell division.

Ionising radiation comprises highly-energetic particles or waves that can detach at least one electron from an atom or molecule, thereby ionising it. Ionising ability is a function of the energy of individual particles or waves, and not a function of their number. A large number of particles or waves will not, in the most common situations, cause ionisation if the individual particles or waves are insufficiently energetic.

Examples of ionising radiation are energetic beta particles, neutrons, and alpha particles. X-rays and gamma-rays will ionise almost any molecule or atom; far ultraviolet light will ionise many atoms and molecules; near ultraviolet and visible light are ionising to very few molecules; microwaves and radio waves are non-ionising forms of radiation.

The symptoms of radiation exposure may vary but can present with nausea and vomiting; diarrhea; skin burns (radiodermatitis); weakness; fatigue; loss of appetite; fainting; dehydration; inflammation (swelling, redness or tenderness) of tissues; bleeding from your nose, mouth, gums or rectum; low red blood cell count (anaemia) and hair loss. The signs and symptoms of radiation exposure depend on how much radiation has been received and which tissues are exposed. Exposure to a radioactive source is also used in the treatment of cancer. Such exposure can also cause temporary chronic radiation poisoning.

At present it is not possible to reverse the effects of radiation exposure. Anaesthetics and antiemetics are administered to counter the symptoms of exposure, together with antibiotics for countering secondary infections due to the resulting immune system deficiency. Blood transfusions may also be necessary if anaemia develops.

Drugs approved by the Food and Drug Administration (FDA) for treatment of radiation contamination from an industrial accident or a dirty bomb include Radiogardase, pentetate calcium trisodium (Ca-DTPA) and pentetate zinc trisodium (Zn-DTPA). Radiogardase, also known as insoluble Prussian Blue, may be used to treat people exposed to radiation containing harmful amounts of cesium-137 or thallium. Ca-DTPA and Zn-DTPA may be used for contamination with radioactive forms of plutonium, americium and curium. All three drugs work to eliminate radioactive substances from the human body.

Another drug that may be helpful in cases of exposure to high doses of radiation is filgrastim (Neupogen), a drug currently used in people who have received chemotherapy or radiation therapy. This drug stimulates the growth of white blood cells and can help repair bone marrow damage.

It is an object of the present invention to overcome or ameliorate at least some of the deficiencies of the prior art or to provide a useful alternative.

SUMMARY OF THE INVENTION

The present invention is in part based on a surprising observation that a muramyl dipeptide cross-linked into a microparticle (MDP-microparticle) is capable of inducing de novo synthesis of immunomodulatory cytokines that are known to have clinical utility in either preventing haematopoietic or bone marrow damage, or accelerating bone marrow restoration following exposure to radiation, particularly ionising radiation. Further, the MDP-microparticle may be functionalised with one or more ligands capable of enhancing de novo synthesis of immunomodulatory cytokines, thus enhancing the prevention or repair of damage due to exposure to radiation such as ionising or other radiation.

According to a first aspect, the present invention provides a method of prophylactic or therapeutic treatment of exposure to ionising radiation or radiation poisoning comprising administrating an effective amount of an MDP-microparticle or a composition comprising an MDP-microparticle to a subject requiring such treatment.

Accordingly, in a second aspect, the present invention provides a method of accelerating bone marrow restoration in a subject exposed to radiation or having radiation poisoning comprising administrating an effective amount of an MDP-microparticle or a composition comprising an MDP-microparticle to the subject requiring such treatment.

Accordingly, in a third aspect, the present invention provides a method of accelerating myelorestoration in a subject exposed to radiation or having radiation poisoning comprising administrating an effective amount of an MDP-microparticle or a composition comprising an MDP-microparticle to the subject requiring such treatment.

According to a fourth aspect the present invention provides a method of stimulating release of cytokines in a subject exposed to radiation or having radiation poisoning comprising administering an effective amount of an MDP-microparticle or a composition comprising an MDP-microparticle to a subject requiring such treatment.

Accordingly, in a fifth aspect, the present invention provides a method of inducing thrombocytosis in a subject exposed to radiation or having radiation poisoning comprising administrating an effective amount of an MDP-microparticle or a composition comprising an MDP-microparticle to the subject.

The MDP-microparticle may be combined with at least one immunostimulatory ligand, bound to or associated with the microparticle, that is capable of stimulating de novo synthesis of immunomodulatory cytokines that are known to either prevent haematopoietic damage or accelerate bone marrow restoration following exposure to ionising radiation. Suitable ligands may be selected from known ligands of described pathogen molecular pattern recognition receptors including TLR1, 2, 3, 4, 5, 6, 7, 8, 9, 10, NOD-1, NOD-2 and the like. Other useful receptors are well known in the art and can be easily identified by those skilled in the art.

Preferably, the at least one immunostimulatory ligand is cross-linked on the surface of the MDP-microparticle.

Preferably, the MDP-microparticle stimulates the production of granulocyte-macrophage colony-stimulating factor (GM-CSF). Most preferably, the MDP-microparticle stimulates the production of both GM-CSF and interleukin-3 (IL-3).

It is an advantage that the MDP-microparticle also stimulates the production of interleukin-1 (IL-1), interleukin-6 (IL-6) and tumour necrosis factor-α (TNFα).

Advantageously, the MDP-microparticle, or a composition containing the MDP-microparticle, may be used to prevent and/or ameliorate radiation toxicity associated with radiotherapy such as that used in cancer therapy. In this instance, the MDP-microparticle or composition thereof may be administered up to 7 days prior to radiation therapy. More preferably, the MDP-microparticle or composition thereof may be administered 24 hours prior to radiation therapy. More preferably, the MDP-microparticle or composition thereof may be administered 30 minutes prior to radiation therapy. Of course, it will be appreciated by those of skill in the art that the MDP-microparticle or a composition thereof may be administered at any time prior to the commencement of radiation therapy or during radiotherapy, as the situation demands. It is also envisioned that the MDP-microparticle or composition may be administered to a patient who has finished a course of radiotherapy.

For the treatment of unexpected radiation exposure, the MDP-microparticle is preferably administered immediately after exposure to a source of radiation. More preferably, the MDP-microparticle may be administered within at least 5 minutes of the exposure. Most preferably, the MDP-microparticle may be administered from about 1 minute to about 2 hours after exposure to the source of radiation.

Alternatively the MDP-microparticle is administered within about 24 hours after radiation exposure.

Radiation poisoning may be caused by exposure to radioactivity by inhalation, ingestion or by direct external exposure.

Radiation poisoning may be caused by exposure to a source of ionising radiation. The source of ionising radiation may be, for example, alpha particles, beta particles, neutrons, X-rays or gamma-rays.

Exposure to radiation may be occupational but may also be a result of a therapeutic procedure such as, for example, radiotherapy.

Advantageously, the MDP-microparticle may be used in combination with one or more other agents for the treatment of radiation exposure or radiation poisoning. The one or more other agents for the treatment of radiation exposure or radiation poisoning may be selected from insoluble Prussian Blue, Ca-DTPA, Zn-DTPA, filgrastim or hormones and cytokines, for example, IL-1, IL-3, IL-6, GM-CSF and TNFα. The treatments of the present invention may also be combined with procedures such as bone marrow transplant or blood transfusion.

Preferably, the MDP-microparticle may be used as a co-therapy in combination with the one or more other agents for the treatment of radiation exposure or radiation poisoning. Alternatively, the one or more other agents for the treatment of radiation exposure or radiation poisoning may be used in adjunctive therapy with the MDP-microparticle. Such therapy may include administration of the agent and the MDP-microparticle simultaneously or sequentially.

Sequential administration may be separated by any suitable time-frame of minutes, hours, days or weeks. It will be appreciated that the above list of treatments for radiation exposure or radiation poisoning is not exhaustive and that other agents can be used as a co-therapy or adjunctive therapy together with the MDP-microparticle.

It will be further appreciated that the MDP-microparticle may be formulated with a pharmaceutically acceptable carrier. Suitable carriers and formulations will be known to those of skill in the art or obtainable from, for example, Remington: The Science and Practice of Pharmacy, $19^{th}$ Ed 1995 (Mack Publishing Co. Pennsylvania, USA), British Pharmacopoeia, 2000, and the like.

While not wishing to be bound by any particular theory as to how the present invention works, it is believed that the ability of the MDP-microparticle to treat radiation exposure or radiation poisoning arises from the demonstrable stimulation of cells within the reticuloendothelial system to secrete cytokines, for example, GM-CSF, IL-1, IL-6 and TNFα, which are known to accelerate bone marrow restoration and myelorestoration. Preferably, the cytokines are selected from IL-1, IL-3, IL-6, GM-CSF or TNFα.

The MDP-microparticle may be administered intravenously. Alternatively, the MDP-microparticle may be administered by other routes, for example orally, intramuscularly, intranasally, by nebulization or dry powder administration directly to the airways of a lung or nasal mucosa. The MDP-microparticle may be administered at a dose of from about 1 μg to about 150 μg/Kg bodyweight, preferably from about 1 μg to about 15 μg/Kg body weight for prophylactic and therapeutic intervention to prevent or ameliorate effects of radiation exposure or radiation toxicity. Of course any dosage amount within this range would also be useful. Doses in a higher range can also be used depending on the requirements, for example doses selected in the range from about 1 to about 20 mg/Kg body weight, or any suitable dose within this range, may be suitably used. Of course, those skilled in the art will appreciate that the route of administration and dose may vary significantly depending on a therapeutic verus prophylactic application, as well as the dose of radiation received, the condition of the patient and other measurable laboratory parameters such as blood counts and the like.

The radiation that affects a subject may be ionising radiation but may also be cosmic or solar radiation. More specifically the radiation may be radio waves, electromagnetic waves, infrared rays, visible light, ultraviolet rays such as ultraviolet-A, ultraviolet-B or ultraviolet-C, alpha rays, beta rays, proton beams, baryon beams, X-rays, gamma rays, electron beams, neutron beams and the like. Exposure to radiation can also be caused by radiation therapy such as that used for treatment of cancer.

In prophylactic use, the MDP-microparticle can stimulate the reticuloendothelial system and other cells of the immune and endocrine system to secrete cytokines that can protect a subject from lethal doses of radiation. Alternatively, the MDP-microparticle may be used as a radiotherapy protectant during the treatment of cancer using radiotherapy.

Preferably, the cytokines are selected from GM-CSF, IL-1, IL-6, and TNFα.

According to a sixth aspect, the present invention provides a MDP-microparticle or a composition comprising an MDP-microparticle for the prophylactic or therapeutic treatment of radiation exposure or radiation poisoning in a subject exposed to radiation or having radiation poisoning.

According to a seventh aspect, the present invention provides a MDP-microparticle or a composition comprising an MDP-microparticle for accelerating bone marrow restoration in a subject exposed to radiation or having radiation poisoning.

According to an eighth aspect, the present invention provides a MDP-microparticle or a composition comprising an MDP-microparticle for accelerating myelorestoration in a subject exposed to radiation or having radiation poisoning.

According to a ninth aspect, the present invention provides a MDP-microparticle or a composition comprising an MDP-microparticle for stimulating release of cytokines in a subject exposed to radiation or having radiation poisoning.

According to a tenth aspect, the present invention provides a MDP-microparticle or a composition comprising an MDP-microparticle for inducing thrombocytosis in a subject exposed to radiation or having radiation poisoning.

In the context of the present invention, the terms "MIS", "MIS(416)" and "MDP-microparticle" may be used interchangeably.

In the context of the present invention, the term "therapeutic" is intended to mean curative treatment of an existing condition, and the term "prophylactic" is intended to mean protecting or preventing from disease or condition developing or at least not developing fully.

"Bone marrow restoration" refers generally to restoration of normal function of the bone marrow, for example the restoration of red marrow (consisting mainly of myeloid tissue) and yellow marrow (consisting mainly of fat cells) i.e. the tissue that fills the cavities of bones and produces new blood cells. "Myelorestoration" refers to the restoration of tissue within marrow that produces blood cells. "Thrombocytosis" refers to enhancement of platelet production and/or replenishment of platelet count in the blood. "Hematopoietic reconstitution" refers to the reconstitution of cellular blood components that are derived from haematopoietic stem cells. Haematopoietic stem cells reside in the medulla (bone marrow) and have the unique ability to give rise to all of the different mature blood cell types. "Erythropoiesis" refers to the process by which red blood cells (erythrocytes) are produced. In human adults, this usually occurs within the bone marrow. In the context of the present invention, administration of the MDP-microparticle in the treatment of radiation exposure or radiation poisoning is intended to preserve, accelerate, stimulate or induce the processes mentioned above.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

BRIEF DESCRIPTION OF THE DRAWINGS

A preferred embodiment of the invention will now be described, by way of example only, with reference to the accompanying drawings, in which.

DESCRIPTION OF THE PREFERRED EMBODIMENT

Figure 1:
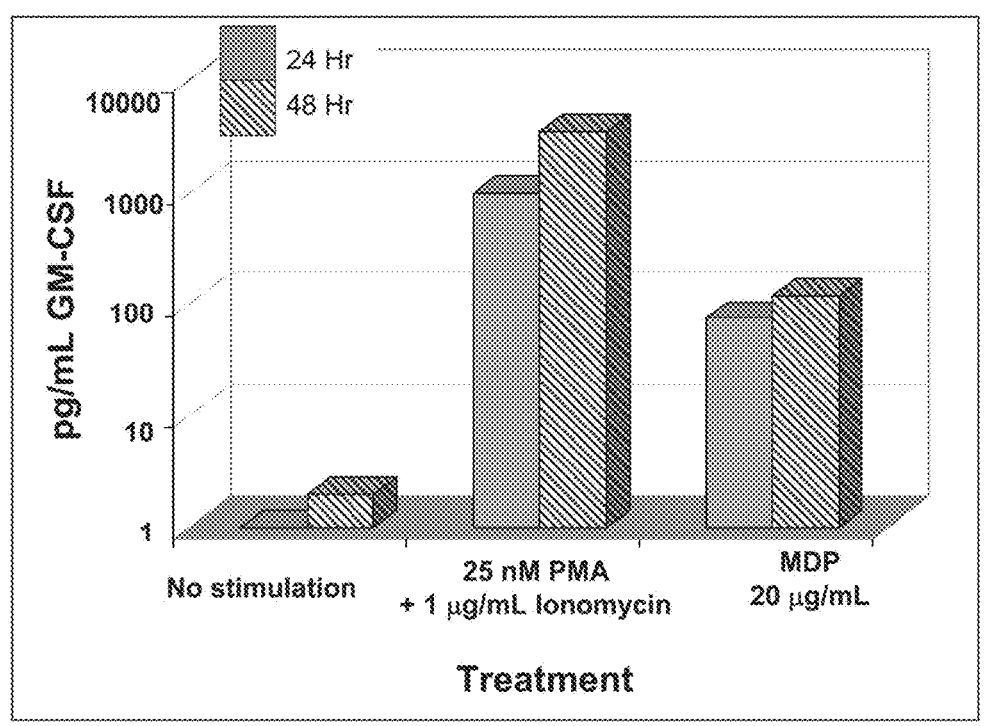
FIG. 1 is a graph showing in vitro production of GM-CSF following stimulation of human whole blood with MDP-microparticles.

Previously, applicant has disclosed an immunostimulant in the form of a muramyl dipeptide microparticle for the treatment of HIV and Anthrax in Australian Patent No. 732809 and International Patent Application No. PCT/NZ2008/000131, respectively. However, applicant has surprisingly and unexpectedly found that a muramyl dipeptide microparticle is useful in the treatment of exposure to toxic levels of radiation, both when administered before and following radiation exposure.

The present invention is in part based on a surprising observation that a muramyl dipeptide cross-linked into a microparticle (MDP-microparticle) is capable of inducing de novo synthesis of immunomodulatory cytokines that are known to have clinical utility in either preventing haematopoietic damage or accelerating bone marrow restoration following exposure to ionizing radiation. Further, the MDP-microparticle may be functionalised with one or more ligands capable of enhancing de novo synthesis of immunomodulatory cytokines, thus enhancing the prevention or repair of damage due to exposure to ionizing radiation.

The present invention provides methods of prophylactic or therapeutic treatment of exposure to radiation, particularly ionising radiation, or radiation poisoning comprising administrating an effective amount of an MDP-microparticle or a composition comprising an MDP-microparticle to a subject requiring such treatment.

To enhance the prevention or repair of damage due to exposure to radiation such as ionising radiation, the MDP-microparticle may be combined with one or more immunostimulatory ligands, bound to or within the microparticle, that is(are) capable of stimulating de novo synthesis of immunomodulatory cytokines that are known to either prevent haematopoietic damage or accelerate bone marrow restoration following exposure to ionising radiation. Suitable ligands may be selected from known ligands of described pathogen molecular pattern recognition receptors including TLR1, 2, 3, 4, 5, 6, 7, 8, 9, 10, NOD-1, NOD-2 and the like. Other useful receptors are well known in the art and can be easily identified by those skilled in the art. Other useful immunostimulatory ligands are well known in the art and can be easily identified by those skilled in the art, such as heat-shock proteins and glycolipid antigens.

The immunostimulatory ligand(s) if used may be cross-linked on the surface of, or otherwise associated with, the MDP-microparticle but it will be understood that they may also be co-administered with the MDP-microparticle.

Without wishing to be bound by theory or any particular mechanism of action henceforth, the MDP-microparticle and its compositions stimulate the production of inter alia granulocyte-macrophage colony-stimulating factor (GM-CSF) or the production of both GM-CSF and interleukin-3 (IL-3). This is advantageous, since IL-3 is known to act co-operatively with GM-CSF as a haematopoietic cytokine. Advantageously the MDP-microparticle may also stimulate the production of interleukin-1 (IL-1), interleukin-6 (IL-6) and tumour necrosis factor-α (TNFα).

The MDP-microparticle may also stimulate hematopoietic reconstitution by increasing the production of white blood cells and platelets or stimulate erythropoiesis by increasing the production of red blood cells.

Advantageously, the MDP-microparticle, or a composition containing the MDP-microparticle, may be used to prevent and/or ameliorate radiation toxicity associated with radiotherapy. It will be appreciated by those of skill in the art that the MDP-microparticle or a composition thereof, when used for this purpose, may be administered at any time prior to the commencement of radiation therapy or during radiotherapy. The MDP-microparticle or composition thereof may be administered up to 7 days prior to radiation therapy but in practice, and for preference, it may be administered between 24 hours and 30 minutes prior to radiation therapy. It is also envisioned that the MDP-microparticle or composition may be administered to a patient who has finished a course of radiotherapy and achieve the desired beneficial effects.

For the treatment of unexpected radiation exposure, the MDP-microparticle is preferably administered immediately after exposure to a source of radiation. The MDP-microparticle may be administered from about 1 minute to about 2 hours after exposure to the source of radiation, or alternatively 24 hours after exposure. For preference, the MDP-microparticle may be administered within about 5 minutes of the exposure.

Radiation poisoning may be caused by exposure to radioactivity/source of ionising radiation by inhalation, ingestion or by direct external exposure. The source of ionising radiation may be, for example, alpha particles, beta particles, neutrons, X-rays or gamma-rays.

Exposure to radiation may be occupational but may also be a result of a therapeutic procedure such as, for example, radiotherapy such as used in the treatment of cancer.

Advantageously, the MDP-microparticle may be used in combination with one or more other agents for the treatment of radiation exposure or radiation poisoning. Such other agents for the treatment of radiation exposure or radiation poisoning may be selected from insoluble Prussian Blue, Ca-DTPA, Zn-DTPA, filgrastim, or hormones and cytokines, for example, IL-1, IL-3, IL-6, GM-CSF and TNFα. The treatments of the present invention may also be combined with procedures such as bone marrow transplant and blood transfusion.

Alternatively, the one or more other agents for the treatment of radiation exposure or radiation poisoning may be used in adjunctive therapy with the MDP-microparticle. Such therapy may include administration of the agent and the MDP-microparticle simultaneously or sequentially. Sequential administration may be separated by any suitable time-frame of minutes, hours, days or weeks.

It will be appreciated that the above list of treatments for radiation exposure or radiation poisoning is not exhaustive and that other agents can be used as a co-therapy or adjunctive therapy together with the MDP-microparticle.

It will be further appreciated that the MDP-microparticle may be formulated with a pharmaceutically acceptable carrier. Suitable carriers and formulations will be known to those of skill in the art or obtainable from, for example, Remington: The Science and Practice of Pharmacy, 19$^{th}$ Ed, 1995 (Mack Publishing Co. Pennsylvania, USA), British Pharmacopoeia, 2000, and the like.

The MDP-microparticle of the present invention is resistant to treatment with pepsin and extremes of pH and denaturing conditions, such as for example treatment with pepsin at pH 3.5, or pH of less than 1 and greater than 11 at ambient temperature, or denaturing conditions in 6 M urea or 6 M guanidine hydrochloride.

While not wishing to be bound by any particular theory as to how the present invention works, it is believed that the ability of the MDP-microparticle to treat radiation exposure or radiation poisoning arises from the demonstrable stimulation of cells within the reticuloendothelial system to secrete cytokines, for example, GM-CSF, IL-1, IL-6 and TNFα, which are known to accelerate bone marrow restoration and myelorestoration.

The present invention therefore also encompasses methods of accelerating bone marrow restoration, accelerating myelorestoration and/or stimulating release of cytokines in a subject exposed to radiation or having radiation poisoning comprising administrating an effective amount of an MDP-microparticle to the subject requiring such treatment.

Preferably, the cytokines are selected from IL-1, IL-3, IL-6, GM-CSF or TNFα. The MDP-microparticle may be administered intravenously but may also be administered by other routes, for example orally, intramuscularly, intranasally, by nebulization or dry powder administration directly to the airways of a lung or nasal mucosa. The MDP-microparticle may be administered at a dose of from 1 μg to 150 μg/Kg body weight for prophylactic and therapeutic intervention to prevent or ameliorate effects of exposure to radiation. Typically, the MDP-microparticle or its composition may be administered at a dose of from about 1 μg to about 150 μg/Kg bodyweight, preferably from about 1 μg to about 10 μg/Kg body weight for prophylactic and therapeutic intervention to prevent or ameliorate effects of radiation exposure or radiation toxicity. The MDP-microparticle can also be administered at intermediate doses selected from about 1, 3, 5, 7, 10, 12, 15, 17, 20, 25, 30, 35, 40, 45, 50, 55, 60, 65, 70, 75, 80, 85, 90, 95, 100 or 150 μg/Kg body weight. Doses in a higher range can also be used depending on the requirements, for example doses selected from of about 1, 3, 5, 7, 10, 13, 15, 17 or 20 mg/Kg body weight. Of course, those skilled in the art will appreciate that the route of administration and dose may vary significantly depending on a therapeutic verus prophylactic application, as well as the dose of radiation received, the condition of the patient and other measurable laboratory parameters such as blood counts and the like. The treatment may comprise a single daily does, multiple daily doses or doses administered less frequently such as bi-daily, weekly or monthly.

The compositions and methods of the present invention are effective for treatment (prophylactic or therapeutic, i.e. preventive or curative) of exposure to a variety of radiation sources, such as for example ionising radiation, solar radiation, cosmic radiation, external terrestrial sources, and radon. Ionising radiations exist for example, as alpha particles, beta particles, neutrons, and in some cases, photons. Ultraviolet, x-rays and gamma rays are some examples of known forms of ionising radiation. Several sources of ionising radiation include, but are not limited to radioactive materials, x-ray tubes, and particle accelerators. Exposure to ionising radiation can cause damage to living tissues and can result in radiation sickness and skin burn. High enough doses of ionising radiation can also result in development of cancers and tumours, and in extreme cases can even result in death. Low doses have been shown to cause genetic damage by breaking one or both DNA strands or by forming free radicals. Ionizing radiation can also be used for medical purposes i.e. as part of cancer treatment to control malignant cells. Solar radiation describes the visible and near-visible (ultraviolet and near-infrared) radiation emitted from the sun. The ionizing component of solar radiation is negligible relative to other forms of radiation on the Earth's surface. However, excessive exposure to the ultraviolet part of radiation from sunlight has been linked to many types of skin cancers. Furthermore, sunburn can cause mild inflammation to skin and UV exposure can accelerate skin aging.

More specific examples include cosmic rays, radio waves, electromagnetic waves, infrared rays, visible light, ultraviolet rays (Ultraviolet-A, Ultraviolet-B and Ultraviolet-C), alpha rays, beta rays, proton beams, baryon beams, X-rays, gamma rays, electron beams, neutron beams and the like. Typically, the types of radiation in the present invention are those against which protection is required, for example, cosmic rays, electromagnetic waves, Ultraviolet-A, Ultraviolet-B, alpha rays, beta rays, proton beams, baryon beams, X-rays, gamma rays, electron beams and neutron beams.

In prophylactic use, the MDP-microparticle can stimulate the reticuloendothelial system to secrete cytokines that can protect a subject from lethal doses of radiation. Alternatively, the MDP-microparticle may be used as a radiotherapy protectant during the treatment of cancers using radiotherapy.

Preferably, the cytokines are selected from GM-CSF, IL-1, IL-6, and TNFα. This is advantageous, as these cytokines are known to confer synergistic radioprotection via their individual and complementary mechanisms of action.

Thus the present invention also contemplates methods of inducing thrombocytosis in a subject exposed to radiation or having radiation poisoning comprising administrating an effective amount of an MDP-microparticle to the subject.

The preferred embodiments of the invention will now be described by reference to non-limiting examples.

EXAMPLES

Example 1—Preparation of MDP-Microparticle

A multiple repeat of muramyl dipeptide (MDP) isolated from *Propionibacterium acini*, formed the core structure of the MDP microparticle carrier complex of this example. The chemical composition of the preferred monomeric subunit is as follows:

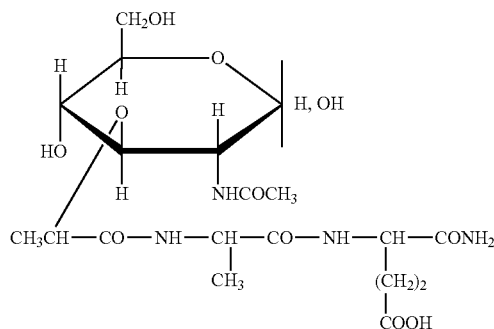

MDP has well known immunostimulatory properties, which have been extensively evaluated in studies designed to determine its effect on increasing immune function. To date, both MDP isolated from natural sources and synthetic MDP have been associated with significant toxicity when administered to mammals. This toxicity has limited the effectiveness of MDP as an adjuvant.

A method for the isolation of MDP, free from toxic components, is provided herein. *Propionibacterium acnes* was grown to a mid-stationary growth phase and washed to remove contaminants of bacterial culture origin employing techniques well known to those in the art. Hydrophobic components contained in the cell walls and cytoplasm were sequentially extracted by successive washes with increasing concentrations of ethanol/isopropanol/water (10%:10%:80%, 25%:25%:50% and 40%:40%:20%) at elevated temperatures. The isopropyl alcohol is then removed with successive washes with decreasing concentrations (80%, 50%, 40% and 20%) of ethanol at elevated temperatures. The resulting MDP-microparticle is then suspended in 20% ethanol and its concentration measured by relating its absorbance at 540 nm to the absorbance of turbidity standards. The concentration of the MDP-microparticle was adjusted to 10 mg/ml for storage and later use.

Analysis of this preparation demonstrated muramyl dipeptide extensively crosslinked with a microparticle size in the range of 0.05 to 0.2 microns. The MDP microparticles contain muramic acid with amino-linked L-alanine-D-isoglutamine dipeptide as the bioactive component. Such a microparticle can be isolated from natural sources, as above, or synthesized using well-known synthetic procedures (for example, Liu G.; Zhang S.-D.; Xia S.-Q.; Ding Z.-K. Bioorganic and Medicinal Chemistry Letters, 10 (12), 2000, pp. 1361-1363(3); Schwartzman S. M., Ribi E., Prep Biochem. 1980; 10(3): 255-67; Ohya et al. Journal of Bioactive and Compatible Polymers, 1993; 8: 351-364). The MDP-microparticles generated by the present methods can have a broad range of sizes (for example, 0.01-2.0 microns) but the preferred size is in the range of 0.05-0.2 microns.

Example 2—Covalent Attachment of Ligands to the MDP-Microparticle

The covalent attachment of a ligand, if used, to the MDP-microparticle can be made through bi-functional cross linkers or to the aldehyde oxidation product of the carbohydrate moiety as disclosed in this examples as described in Current Protocols In Immunology; Series Editor: Richard Coico (Cornell University) Published by John Wiley & Sons, Inc.

MDP-microparticle (20 mg) in 20% ethanol is pelleted by centrifugation, resuspended in and extensively washed with water. The MDP-microparticle is then pelleted and resuspended at a concentration of 50 mg the MDP-microparticle/ml in sodium metaperiodate (0.5M) and an oxidation reaction is carried out for 1 hour at room temperature. Following activation with sodium metaperiodate, the MDP-microparticle suspension is pelleted by centrifugation, resuspended in and extensively washed with water. The concentration of the sodium metaperiodate and the reaction time can be varied to regulate the number of activated sites produced within the MDP-microparticle during oxidation. An activated MDP-microparticle should react with and covalently attach at least one molecule of the subject ligand per MDP-microparticle, preferably 10-100 molecules of subject ligand per MDP-microparticle and most preferably 100 to 1000 subject peptides per MDP-microparticle. For a highly activated MDP-microparticle preparation, a final concentration of 0.5 M sodium metaperiodate is used and the oxidation reaction is carried out for one hour.

Following sodium metaperiodate oxidation, the MDP-microparticle is then pelleted and washed extensively to remove the sodium metaperiodate. The activated MDP-microparticle is then re-suspended in the desired ligand (for example TLR9 or NOD2 at >1 mg/ml at a 20:1 w/w ratio) in sodium bicarbonate buffer (0.1 M pH 9.5) and incubated (ambient temperature) for 18-24 hours. The reactants are centrifuged and the pellet that now contains the ligands linked to the MDP-microparticle through an intermediate Schiff base is reduced to form a stable covalent linkage between the MDP-microparticle and the ligands. Numerous reducing agents can be employed and sodium borohydride is an example of a reducing agent typically used for this purpose. Following reduction of the Schiff base, the MDP-microparticle-ligand conjugate is pelleted, washed and resuspended in the desired vaccine buffer at the desired ligand concentration.

When administration of more than one ligand is desired, a cocktail of ligand MDP-microparticle conjugates can be prepared by mixing individual conjugates at ratios to optimize efficacy of each ligand introduced in the cocktail. In this configuration, sufficient ligand is available on each microparticle conjugate (100-1000 ligands/microparticle) to enhance cellular responses by a single responder cell. Activity of the subject ligand can be optimized by adjusting both the number of subject ligands per MDP-microparticle carrier and, when desired, the ratio of ligands within a cocktail to achieve the desired cellular response.

With multiple repeats of muramyl dipeptide, attachment of the subject ligand to aldehyde groups may be produced by the mild oxidation of sugar residues with, for example, sodium metaperiodate following mild reduction with sodium borohydride and the like. The Schiff's base intermediate is then converted to a stable covalent linkage. The number of ligands per microparticle can be controlled by varying the oxidation conditions and may be quantified as required by employing a radioactive tracer. These methods are well known in the art (for example, Current Protocols in Immunology; Series Editor: Richard Coico (Cornell University) Published by John Wiley & Sons, Inc.).

Example 3—In Vitro Production of GM-CSF Following Stimulation of Human Whole Blood with MDP-Microparticles MDP-microparticles have been shown to induce GM-CSF secretion in diluted whole blood (FIG. 1). GM-CSF levels were determined at T=24 and 88 hr post in vitro stimulation with 20 µg/ml of MDP-microparticles using standard flow cytometric bead array methodology (Becton Dickinson, San Jose, USA). PMA (25 nM) and ionomycin (1 µg/ml) were included for comparison.

Figure 2:
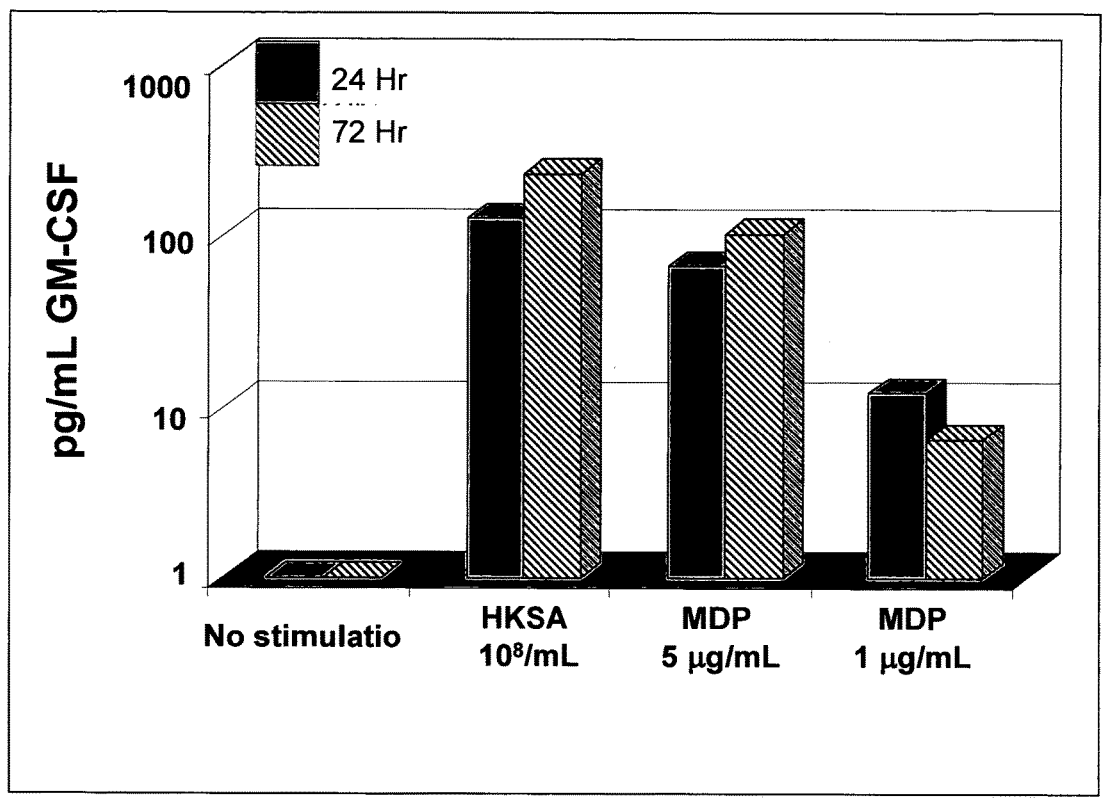
FIG. 2 is a graph showing in vitro production of GM-CSF following stimulation of human PBMC with MDP-microparticles.

Example 4—In Vitro Production of GM-CSF Following Stimulation of Human PBMC with MDP-Microparticles MDP-microparticles have been shown to induce GM-CSF secretion in isolated PBMC stimulation assays (FIG. 2). GM-CSF levels were determined at T=24 and 72 hr post in vitro stimulation with 5 or 1 µg/ml of MDP-microparticles or with 108 particles/ml of HKSA (heat killed *Staphylococcus aureus*) for comparison.

Figure 3:
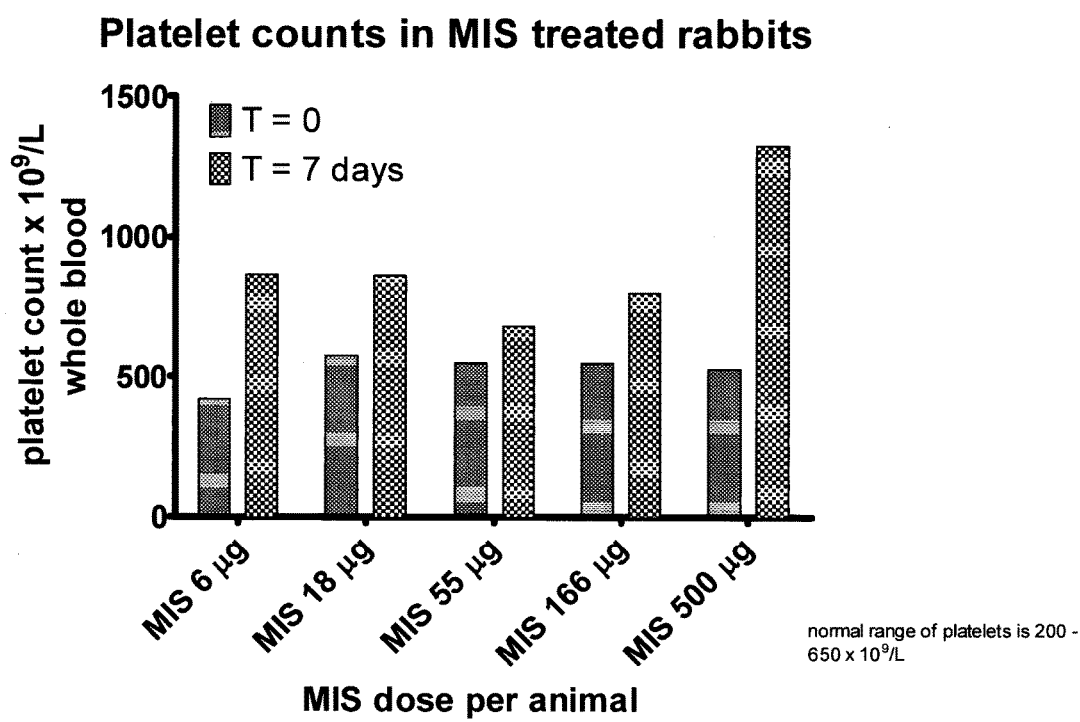
FIG. 3 is a graph showing platelet counts in rabbits treated with varying doses of MDP-microparticles (MIS). The normal range of platelets is 200 to $650 \times 10^9$/L.

Example 5—Rabbit Platelet Counts after Administration of 500 µg i.v. Of MDP-Microparticles MDP-microparticles have been shown to induce thrombocytosis in rabbits seven days after a bolus administration of 500 µg i.v. of MDP-microparticles to rabbits (FIG. 3). This treatment caused a 73% increase in platelet counts (p=0.03 versus untreated controls).

Figure 4:
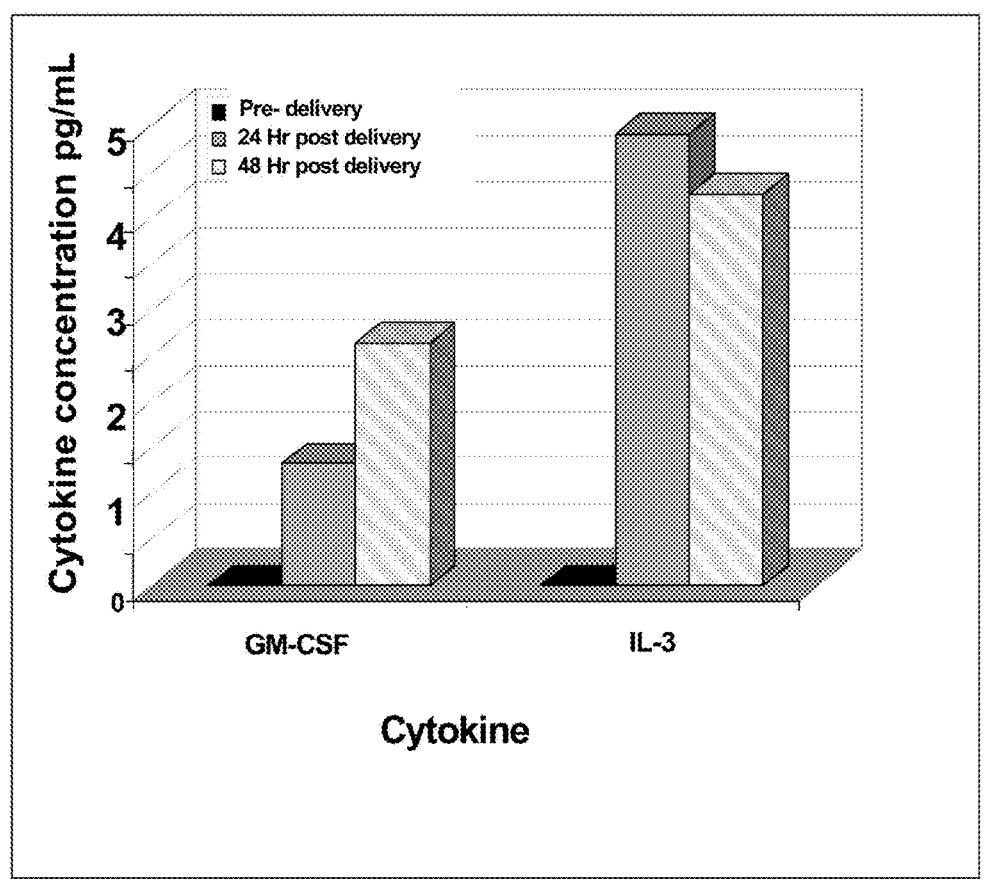
FIG. 4 is a graph showing human peripheral blood serum GM-CSF and IL-3 hematopoietic cytokine levels determined at T=0, 24 and 48 hr post i.v. delivery of 5 mg of MDP-microparticles.

Example 6—Human Peripheral Blood Serum GM-CSF and IL-3 Hematopoietic Cytokine Levels after Administration of 5 mg or 450 µg of MDP-Microparticles Treatment with MDP-microparticles has been found to produce an increase in the levels of GM-CSF as well as IL-3, another hematopoietic cytokine known to act cooperatively with GM-CSF, in the serum of 2 patients. One patient (FIG. 4) received a 5 mg dose of MDP-microparticles (administered in 0.2 mL saline i.v.). Hematopoietic cytokine levels were determined at T=0, 24 and 48 hr post i.v. delivery of 5 mg of MDP-microparticles using standard flow cytometric bead array methodology (Becton Dickinson, San Jose, USA)

Figure 5:
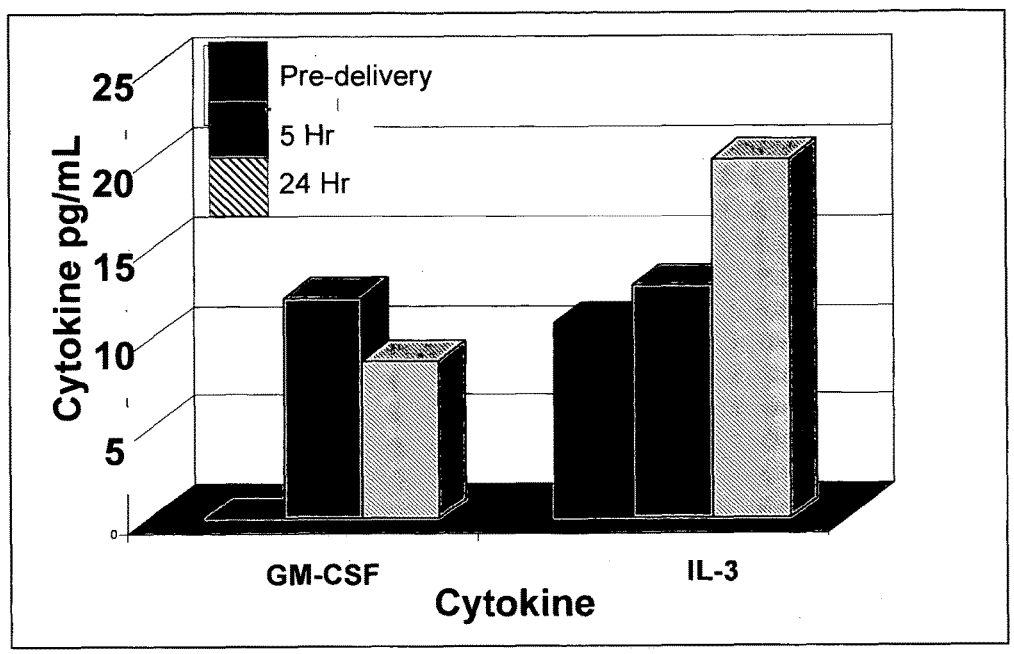
FIG. 5 is a graph showing human peripheral blood serum GM-CSF and IL-3 hematopoietic cytokine levels determined at T=0, 5 and 24 hr post i.v. delivery of 450 µg of MDP-microparticles.

A second patient (FIG. 5) received 450 µg MDP-microparticles (i.v.). hematopoietic cytokine levels determined at T=0, 5 and 24 hr post i.v. delivery of 450 µg of MDP-microparticles.

Figure 6:
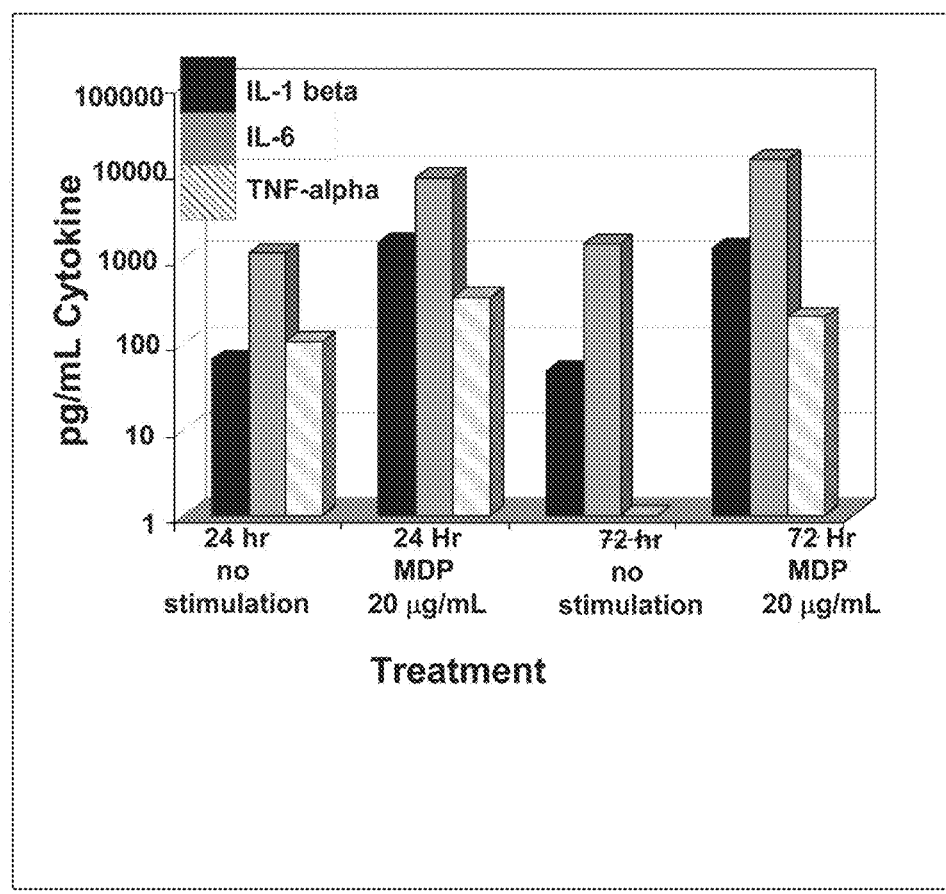
FIG. 6 is a graph showing in vitro production of IL-1 beta, IL-6 and TNF-alpha following stimulation of human PBMC with MDP-microparticles.

Example 7—In Vitro Production of IL-1 Beta, IL-6 and TNF-Alpha Following Stimulation of Human PBMC (Peripheral Blood Mononuclear Cells) with MDP-Microparticles Based on in vitro cell subset uptake data and analysis of the induction of a broad range of cytokines in vitro and in vivo, but without wishing to be bound by any particular mechanism or theory, the data indicates that the MDP-microparticles are acting to stimulate cells within the reticuloendothelial system to secrete cytokines that can accelerate bone marrow restoration or can protect from lethal doses of radiation. In addition to GM-CSF production, associated with myelorestoration, MDP-microparticles have also been shown to induce the production of IL-1, IL-6 and TNFα, cytokines that are known to confer synergistic radioprotection (FIG. 6). Cytokine levels were determined at T=24 and 72 hr post in vitro stimulation with 20 μg/ml of MDP-microparticles using standard flow cytometric bead array methodology (Becton Dickinson, San Jose, USA).

Example 8—Use of MDP-Microparticles as a Radioprotectant when Administered Following Sub-Lethal and Lethal Radiation Exposure Two experiments were performed using different radiation doses—7.2 Gy and 9.0 Gy of gamma radiation from a Cobalt 60 source. This source and type of radiation serves as a useful and convenient generic source of radiation which suitably represents and exemplifies other sources of radiation that may be effectively used or which may be encountered in the environment or be used in therapy or for other purposes.

In both experiments, 24 C57Bl/6 mice were whole body irradiated on day 0 and divided into groups of 12 controls and 12 experimental mice. On day +1, either saline or MDP-microparticles were injected intravenously (250 μg of both, in a volume of 250 μL). This was repeated on day +4, but via subcutaneous injection (100 μg of both—in a volume of 500 μL).

Treatment with MDP-microparticles was given at day +1 to comport with restrictions imposed by the National Institutes of Health guidelines regarding an agent for use in an accidental exposure/terrorist incident.

Experiment 1

Twenty-four C57Bl/6 mice were split into two groups of 12 control and 12 MDP-microparticle treated mice. A sub-lethal dose of 7.2 Gy radiation was then administered on day 0. The mice were weighed on days 0, 4, 8, 10, 11, 14, 16, 17, 18, 19, 20, 21, 22, 23, 24, 25, 26, 28 and 30.

Figure 7:
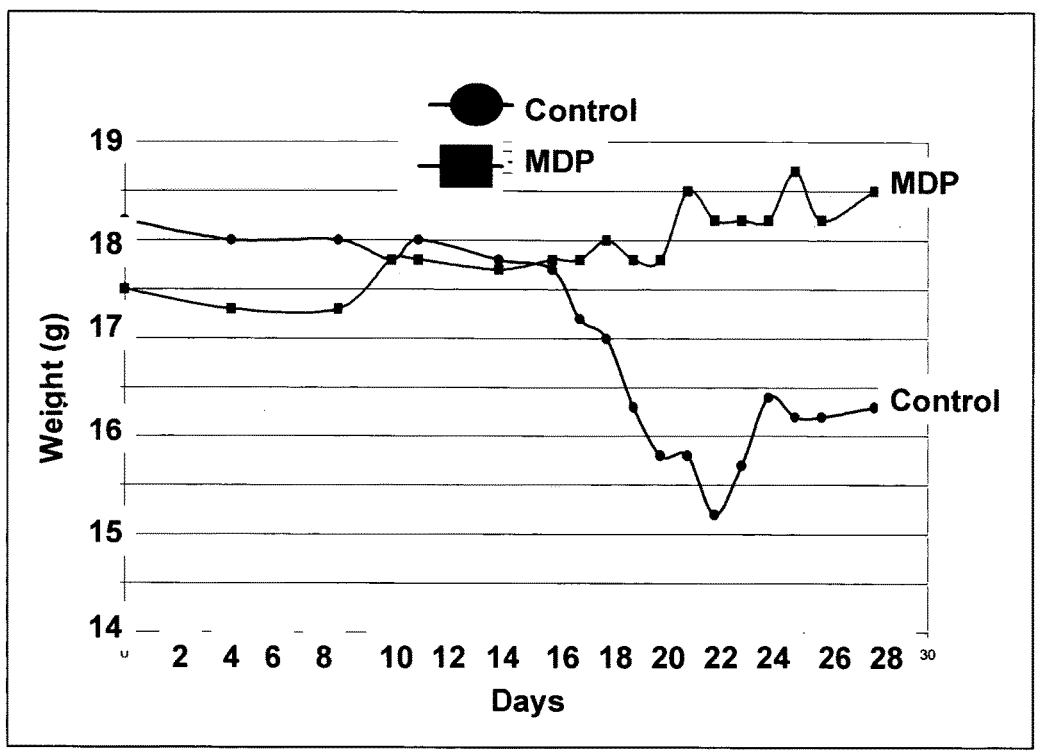
FIG. 7 is a graph showing weight loss in control mice and mice treated with MDP-microparticles following exposure to a non-lethal dose of 7.2 Gy radiation.
Figure 8:
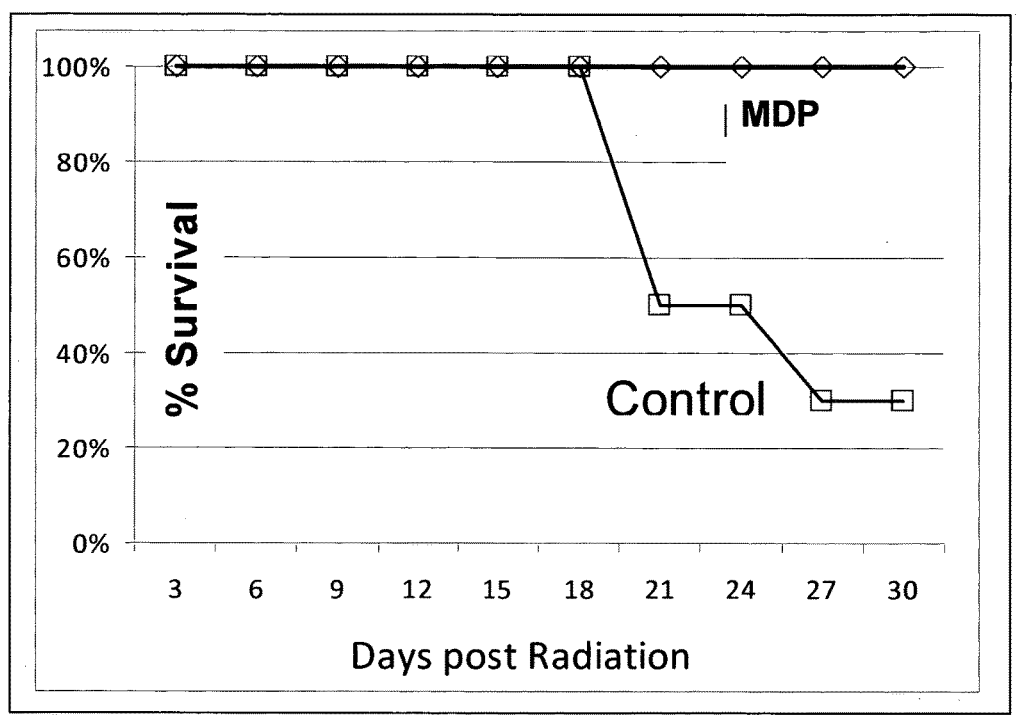
FIG. 8 is a graph showing the survival rate of control mice and mice treated with MDP-microparticles following exposure to a non-lethal dose of 7.2 Gy radiation.

Turning to FIG. 7, the weights of the microparticle treated versus control mice can be seen. It is clear that treatment with MDP-microparticles has prevented the loss of body weight compared with control mice after exposure to a non-lethal dose of radiation FIG. 8 shows the survival rates of control mice and mice treated with MDP-microparticles after exposure to the non-lethal dose of radiation. Mice treated with MDP-microparticles have a better survival rate than the control mice, with 100% of MDP-microparticle treated mice surviving.

Experiment 2

Figure 9:
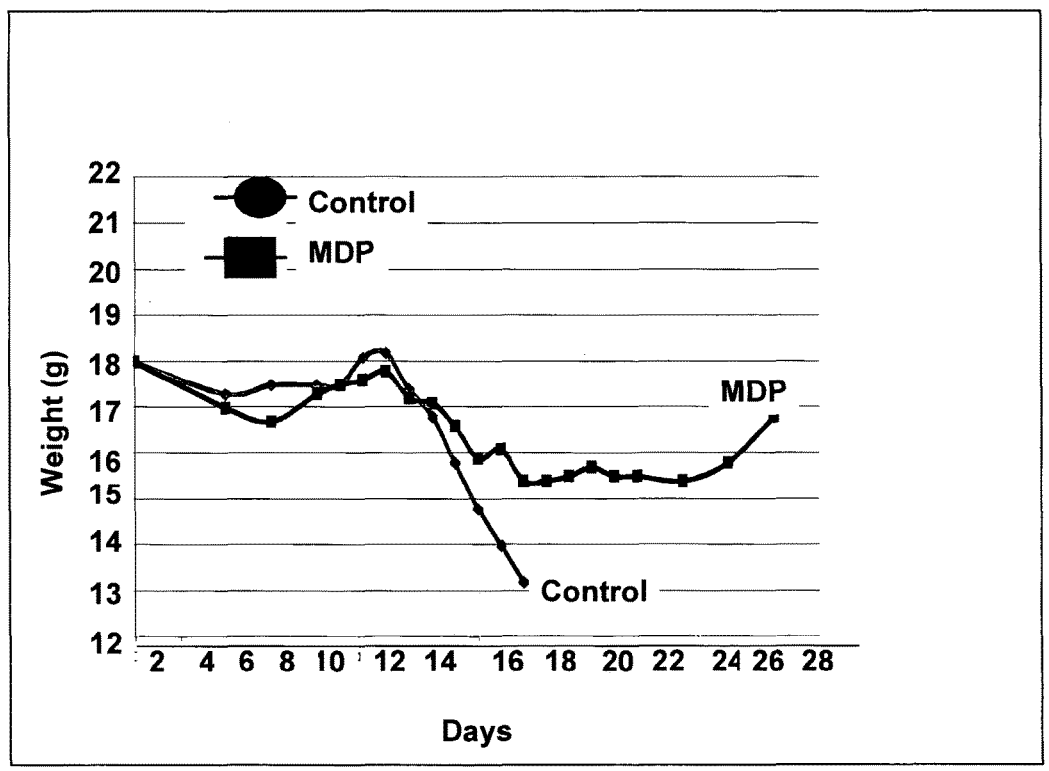
FIG. 9 is a graph showing weight loss in control mice and mice treated with MDP-microparticles following exposure to a lethal dose of 9 Gy radiation.
Figure 10:
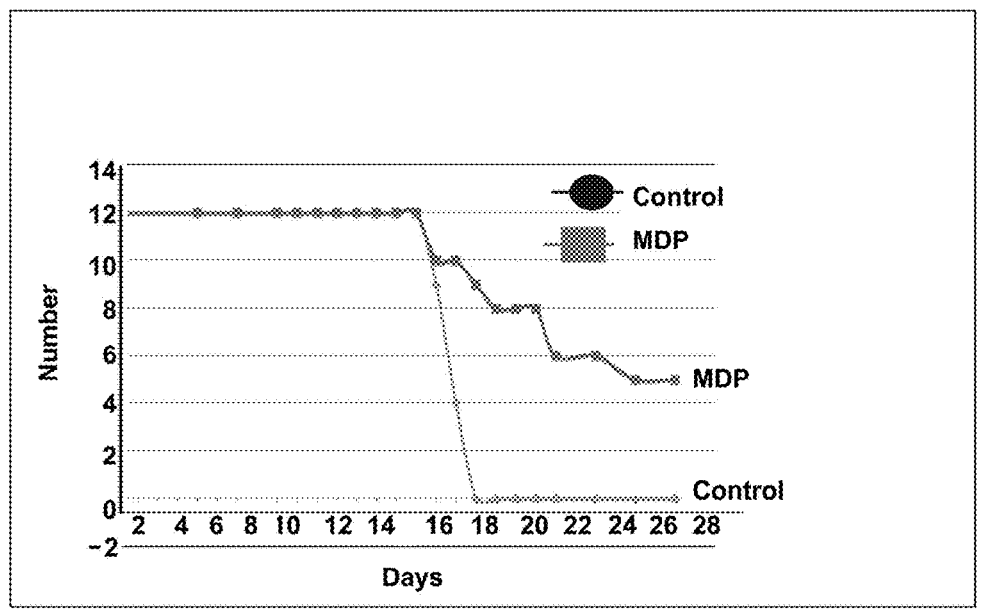
FIG. 10 is a graph showing the survival rate of control mice and mice treated with MDP-microparticles following exposure to a lethal dose of 9 Gy radiation.

As for Experiment 1, twenty-four C57Bl/6 mice were split into two groups of 12 control and 12 MDP-microparticle treated mice. A lethal radiation dose of 9 Gy was administered on day 0. The mice were weighed on days: 0, 4, 6, 8, 9, 10, 11, 12, 13, 14, 15, 16, 17, 18, 19, 20, 21, 22, 24, 26 and 28 and monitored for survival (FIG. 8). FIG. 9 shows the average the weights of the vaccinated versus control mice. It is clear that treatment with MDP-microparticles has prevented the loss of body weight compared with control mice after exposure to the lethal dose of radiation FIG. 10 shows the survival rates of MDP-microparticle treated and control mice irradiated with a lethal dose of radiation. The results clearly show that the mice treated with MDP-microparticles have a greater survival rate than the control mice. All 12 control mice died within 19 days of exposure to lethal radiation.

Example 9—Use of MDP-Microparticles as a Radioprotectant when Administered Prior to as Well as Following Radiation Exposure Experiment 1

CD2F1 male mice, (12 to 14 weeks old) were weighed. Low and high weight animals excluded. The remaining animals were randomized into treatment groups (16 animals per group). Animals were provided with adlib feed (Harlan, Ind.) and acidified water (pH 2.5-3.0). An aliquot of the stock of MDP-microparticle (5 mg/mL) was diluted in saline on the day of injection to deliver 10 mg/kg in 0.1 mL/mouse via the ip (intraperitoneal) route. The experimental animals received 9.0 Gy of whole body irradiation at a dose rate of 0.6 Gy per/min of Cobalt 60 gamma radiation. Drug treated mice were administered 10 mg/kg MDP-microparticle, ip, at −24 hours and +1 hour relative to the time of whole body irradiation.

Figure 11:
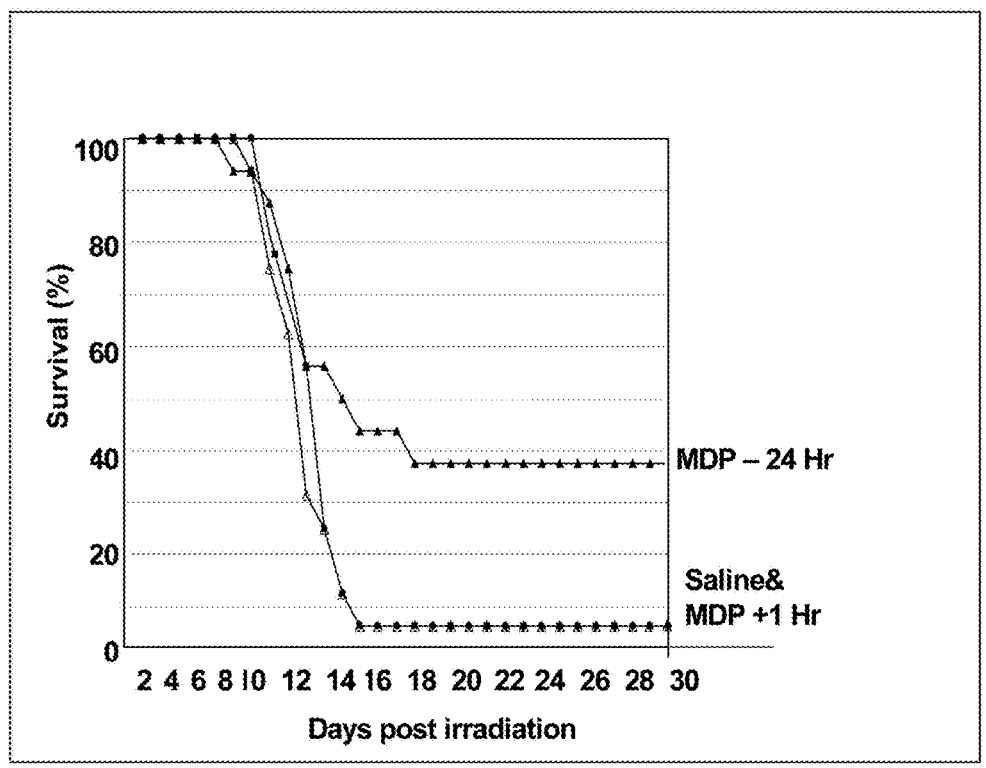
FIG. 11 is a graph showing the survival rate of control mice and mice treated with MDP-microparticles prior to, and following, exposure to a lethal dose of 9 Gy radiation.

FIG. 11 clearly shows that pre-treatment of the mice 24 hours prior to radiation exposure significantly increased their survival. Mice that were not treated with the MDP-microparticles showed an 8% survival rate by 30 days post radiation exposure, whereas mice that were treated ip with MDP-microparticles showed a 38% survival rate.

Experiment 2

C57BL/6 mice (10-12 weeks old) were weighed and the average weight for males and females was determined. Animals were randomized into treatment groups (30 per group). Animals were provided with adlib feed (Harlan 2018C) and acidified water (pH 2.0-3.0). MDP-microparticle (MIS416) was supplied at 1 mg/mL in sterile saline. All female mice were dosed based on the average weight of the females, and all males were dosed based on the average weight of the males. MDP-microparticles were administered by i.p route of injection. The following schedule of administration was performed:
a) 1 dose, 12.5 mg/Kg (250 μg/20 g mouse) 14 days+6 hr before radiation
b) 1 dose, 5 mg/Kg (100 μg/20 mouse) 24±4 hr before radiation
c) 1 dose, 5 mg/Kg (100 μg/20 mouse) 24±4 hr after radiation
d) 2 doses, 5 mg/Kg (100 μg/20 mouse) 24±4 hr before and 24±4 hr after radiation A sub-lethal dose of radiation equal to a LD70/30 (7.96 Gy) was delivered as a single uniform total body dose of gamma radiation from a $_{137}$Cs radiation source at an exposure rate of 0.65-0.69 Gy/minute.

Cell blood counts (CBC) by differential and peripheral smears were performed on 5 randomly selected mice/group in separate cages on day 10 and day 22. CBC's were also performed on 4 non-irradiated age-matched control mice as hematology controls.

Figure 12:
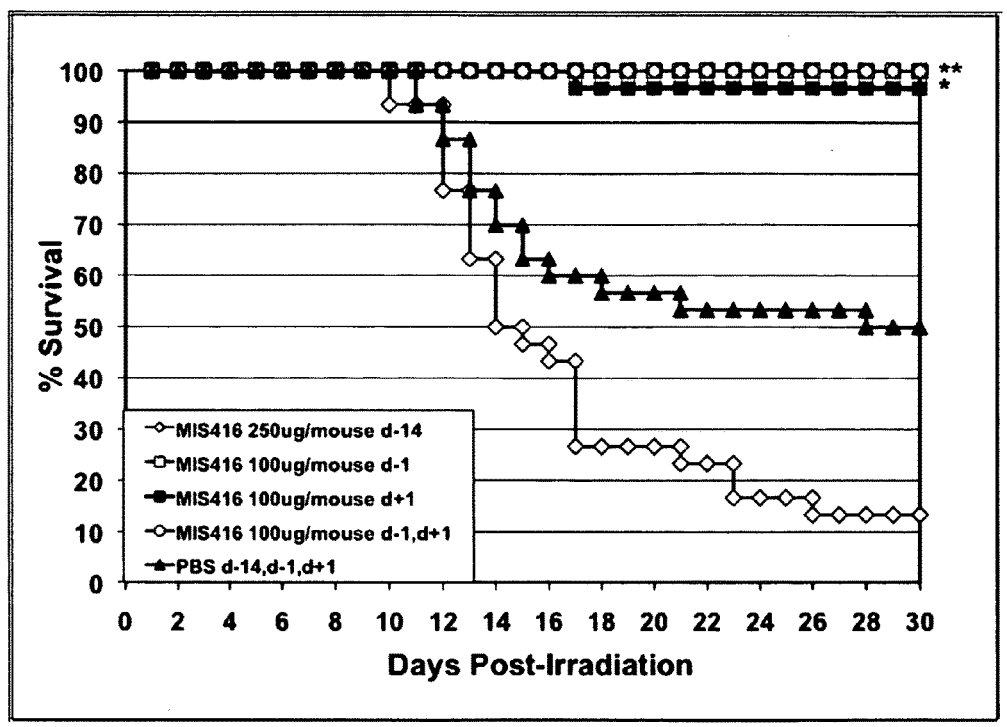
FIG. 12 is a graph showing the survival rate of control mice and mice treated with MDP-microparticles (MIS) prior to, and following whole body exposure to LD70/30 dose (7.96 Gy) of gamma radiation.

The results in FIG. 12 clearly show that the thirty-day survival of mice exposed to 796 cGy radiation and treated with one dose of 5 mg/kg MDP-micropaticles (MIS416) (100 μg/20 g mouse) 24 hr before or 24 hr after irradiation, or two doses of 24 hr before as well as 24 hr after irradiation, was significantly increased compared to controls (survival=100%, 96.7%, 100%, and 50% respectively).

Figure 13:
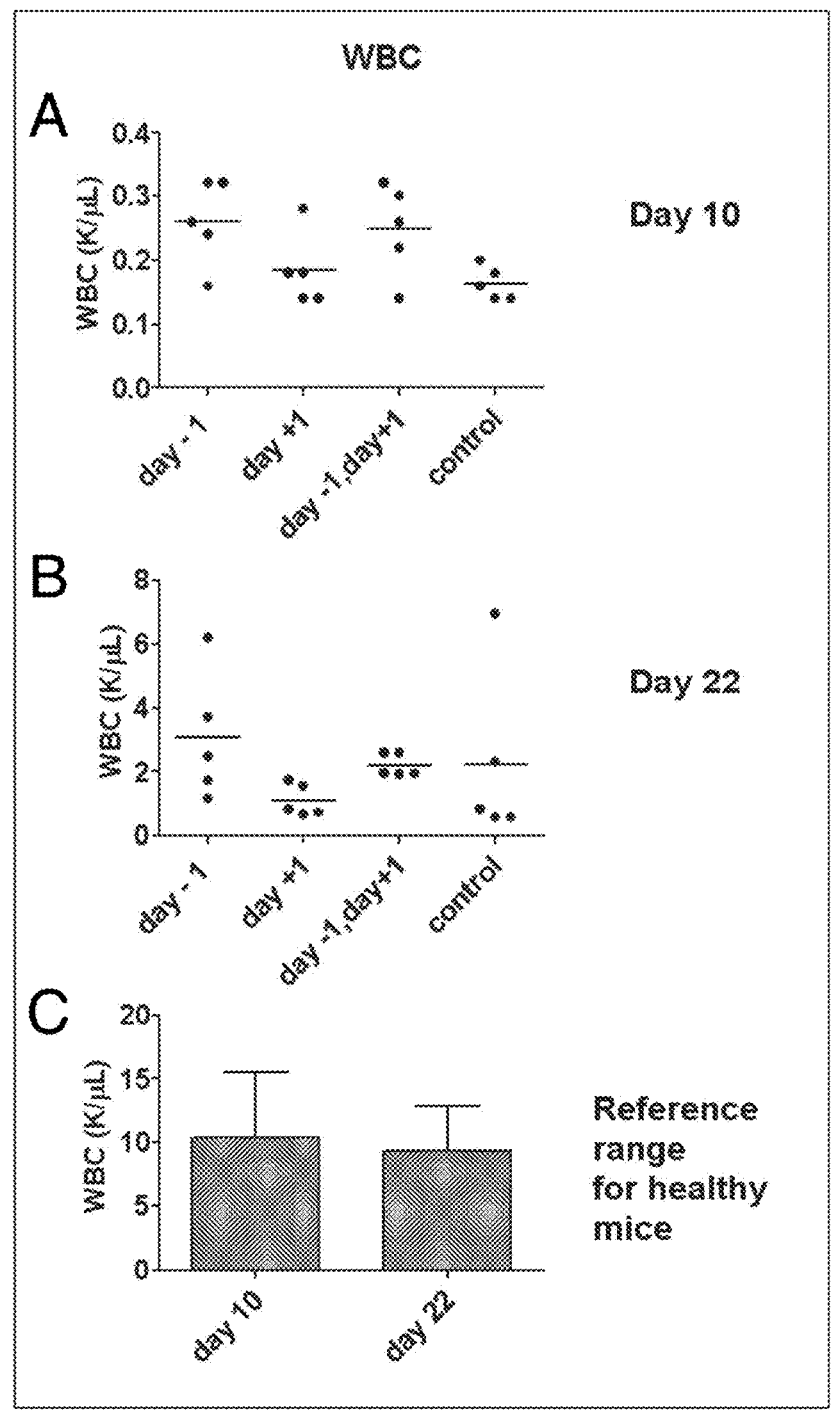
FIGS. 13A-I are graphs showing the immune reconstitution of white blood cells (A-C), neutrophils (D-F) and platelets (G-I) of control mice and mice treated with MDP-microparticles prior to, and following whole body exposure to LD70/30 dose (7.96 Gy) of gamma radiation.
Figure 13:
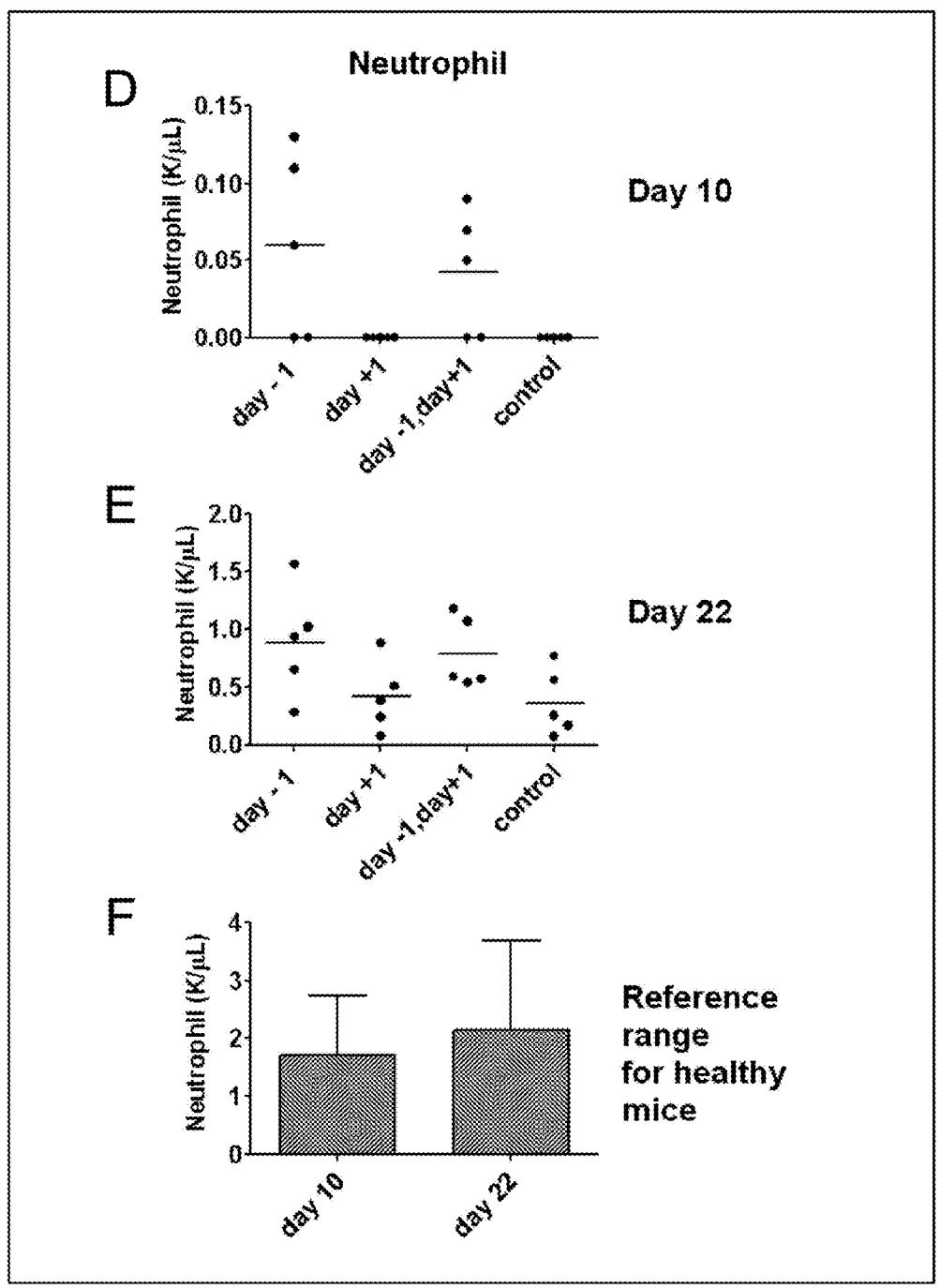
Figure 13:
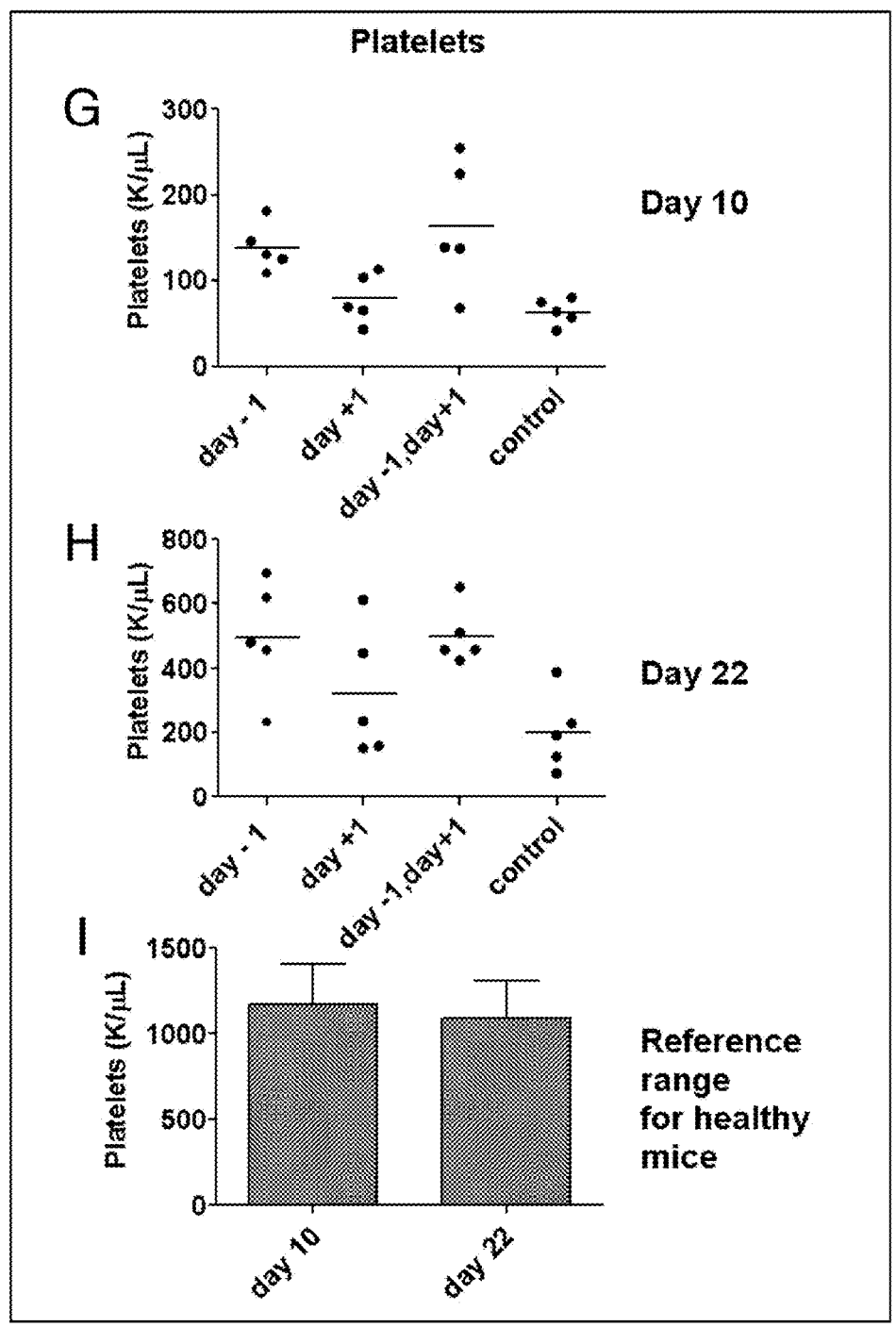

In FIG. 13 the results for CBC leucocyte subset counts show the recovery of white blood cells (WBC), neutrophils (ANC), and platelets was significantly increased on day 10 and 22 in Day-1 and Day-1,+1 MDP-microparticle treated groups compared to controls.

Figure 14:
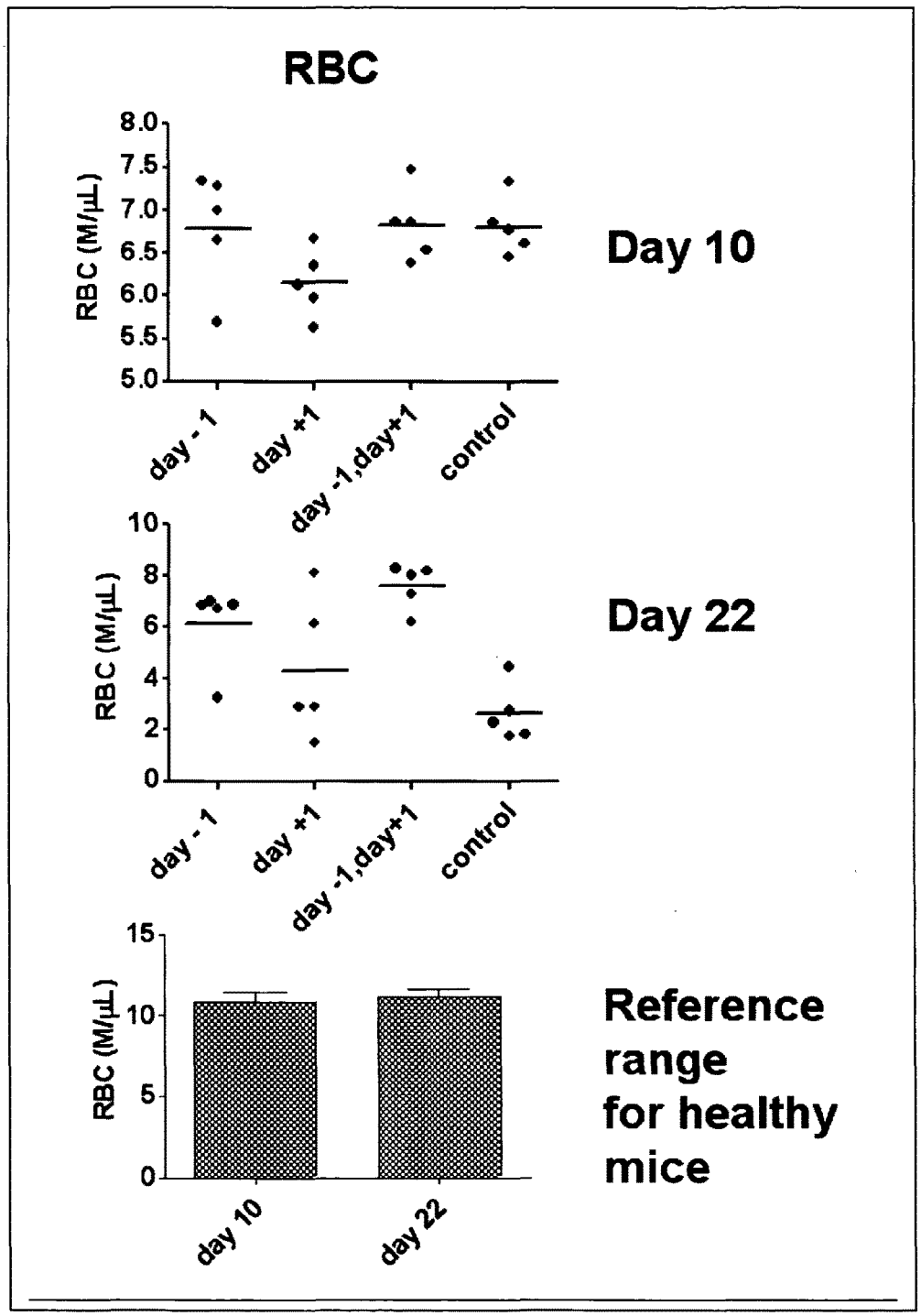
FIG. 14 is a graph showing the reconstitution of red blood cells of control mice and mice treated with MDP-microparticles prior to, and following whole body exposure to LD70/30 dose (7.96 Gy) of gamma radiation.

In FIG. 14, red blood cells (RBC) were significantly increased at day 22 in the Day-1 and Day-1,+1 MDP-microparticle treated groups compared to controls.

Although the invention has been described with reference to certain preferred embodiments and non-limiting examples, variations and modifications in keeping with the spirit of the inventive concept disclosed are also within the scope of the present invention.

The claims defining the invention are as follows:

1. A method of prophylactic or therapeutic treatment of exposure to radiation or radiation poisoning comprising administrating Muramyl dipeptides cross-linked to each other to form a microparticle (MDP-microparticle) or a composition comprising the MDP-microparticle to a subject requiring such treatment in an amount effective to prophylactically or therapeutically treat exposure to radiation or radiation poisoning, wherein the MDP-microparticle is isolated from bacteria.

2. The method according to claim 1, wherein treatment accelerates bone marrow restoration in a subject exposed to radiation or having radiation poisoning.

3. The method according to claim 1, wherein the treatment accelerates myelorestoration in a subject exposed to radiation or having radiation poisoning.

4. The method according to claim 1, wherein the treatment induces thrombocytosis in a subject exposed to radiation or having radiation poisoning.

5. The method according to claim 1, wherein the radiation is ionising radiation or wherein radiation poisoning is caused by ionising radiation.

6. The method according to claim 1, wherein the radiation comprises electromagnetic waves.

7. The method according to claim 1, wherein the MDP-microparticle or a composition comprising the MDP-microparticle is administered intravenously, orally, intramuscularly, intranasally, by nebulization or dry powder administration directly to the airways of a lung or nasal mucosa.

8. The method according to claim 1, wherein the MDP-microparticle or a composition comprising the MDP-microparticle is administered at a dose of from about 1 µg to about 20 mg/Kg body, in single or multiple doses.

9. The method according to claim 8, wherein the MDP-microparticle or a composition comprising the MDP-microparticle is administered at a dose selected from a dosage range of about 1 µg to about 150 µg/Kg body weight.

10. The method according to claim 7, wherein the MDP-microparticle or composition comprising the MDP-microparticle is formulated with a pharmaceutically acceptable carrier.

11. The method according to claim 1, wherein exposure to radiation is caused by radiation therapy.

12. The method according to claim 11, wherein the MDP-microparticle or composition comprising the MDP-microparticle is administered from at least about 24 hours prior to radiation therapy to about 7 days prior to radiation therapy.

13. The method according to claim 11, wherein the MDP-microparticle or composition comprising the MDP-microparticle is administered at least 30 minutes prior to radiation therapy.

14. The method according to claim 11, wherein the MDP-microparticle or a composition comprising the MDP-microparticle is administered at any time prior to the commencement of radiation therapy, at the time of commencement of radiation therapy, during radiotherapy, or after completion of radiation therapy.

15. The method according to claim 1, wherein the MDP-microparticle or a composition comprising the MDP-microparticle is administered immediately after exposure to radiation or from about 1 minute to about 24 hours after exposure to the source of radiation.

16. The method according to claim 1, wherein the MDP-microparticle or a composition comprising the MDP-microparticle is administered within 5 minutes to 2 hours after of the radiation exposure.

17. The method according to claim 1, wherein the MDP-microparticle is combined with at least one immunostimulatory ligand, bound to or associated with the microparticle, that is capable of stimulating immunomodulatory cytokines and wherein the ligand is selected from pathogen molecular pattern recognition receptors TLR1, 2, 3, 4, 5, 6, 7, 8, 9, 10, NOD-1 or NOD-2.

18. The method according to claim 1, wherein the MDP-microparticle stimulates the production of granulocyte-macrophage colony-stimulating factor (GM-CSF), interleukin-3 (IL-3), GM-CSF and interleukin-3 (IL-3), interleukin-1 (IL-1), interleukin-6 (IL-6) and/or tumour necrosis factor-α (TNF α).

19. The method according to claim 1, wherein the MDP-microparticle stimulates hematopoietic reconstitution by increasing the production of white blood cells and platelets and/or stimulates erythropoiesis by increasing the production of red blood cells.

20. The method according to claim 1, wherein the MDP-microparticle is used in combination with one or more other agents for the treatment of radiation exposure or radiation poisoning selected from insoluble Prussian Blue, Ca-DTPA, Zn-DTPA, filgrastim, bone marrow transplant, blood transfusion or hormones and cytokines, and wherein the cytokines are selected from IL-1, IL-3, IL-6, GM-CSF or TNFα.

21. The method according to claim 6, wherein the radiation is selected from radio waves, infrared rays, visible light, ultraviolet rays, and X-rays.

22. The method according to claim 1, wherein the radiation is selected from cosmic rays, alpha rays, beta rays, and gamma rays.

23. The method according to claim 1, wherein the radiation is selected from proton beams, baryon beams, electron beams and neutron beams.

* * * * *